United States Patent [19]
Smith

[11] Patent Number: 5,831,769
[45] Date of Patent: Nov. 3, 1998

[54] PROTECTING EYES AND INSTRUMENTS FROM LASER RADIATION

[76] Inventor: David C. Smith, 44 Candlelight Dr., Glastonbury, Conn. 06033

[21] Appl. No.: 690,292

[22] Filed: Jul. 26, 1996

[51] Int. Cl.[6] .............................. G01B 27/14; G02F 1/03
[52] U.S. Cl. ........................................... 359/634; 359/241
[58] Field of Search ................................ 359/820, 241, 359/243, 634; 372/6, 23, 39, 42

[56] References Cited

U.S. PATENT DOCUMENTS

| | | | |
|---|---|---|---|
| 3,507,552 | 4/1970 | Scott | 359/243 |
| 3,982,206 | 9/1976 | Poulsen | 372/103 |
| 4,595,262 | 6/1986 | Ogle | 359/409 |
| 4,601,533 | 7/1986 | Moss | 359/24 |
| 4,637,678 | 1/1987 | Moss et al. | 359/15 |
| 4,802,719 | 2/1989 | Magarinos et al. | 359/15 |
| 4,830,441 | 5/1989 | Chang | 359/15 |
| 4,879,167 | 11/1989 | Chang | 428/215 |
| 4,917,481 | 4/1990 | Koechner | 359/297 |
| 5,005,926 | 4/1991 | Spielberger | 359/359 |
| 5,448,582 | 9/1995 | Lawandy | 372/42 |
| 5,625,456 | 4/1997 | Lawandy | 356/376 |

OTHER PUBLICATIONS

R. T. Brown and D. C. Smith, "Aerosol–induced thermal blooming", Journal of Applied Physics, vol. 46, No. 1, Jan. 1975, pp. 402–405.

*Primary Examiner*—Georgia Y. Epps
*Assistant Examiner*—Ricky Mack
*Attorney, Agent, or Firm*—M. P. Williams

[57] ABSTRACT

A lens includes a medium which absorbs laser radiation that may be harmful to the eye or other high gain optics, raising its temperature and thereby changing its index of refraction, which causes a phase change in the radiation passing therethrough. The medium may be periodically bounded by thermal sinks, thereby providing a periodic differential in temperature rise, may be provided in a length which varies periodically or may have a density of absorbing material which varies periodically, thereby to have a periodic absorption characteristic. The periodicity, which may be regular or random, provides a periodic variation in total phase change, which causes interference (thermal blooming) that disperses the radiation sufficiently to lower the intensity at the retinal spot below that which would cause damage. Eyeglasses with mutually perpendicular periodicity provide degraded vision of useful images while being protected from harmful radiation.

31 Claims, 5 Drawing Sheets

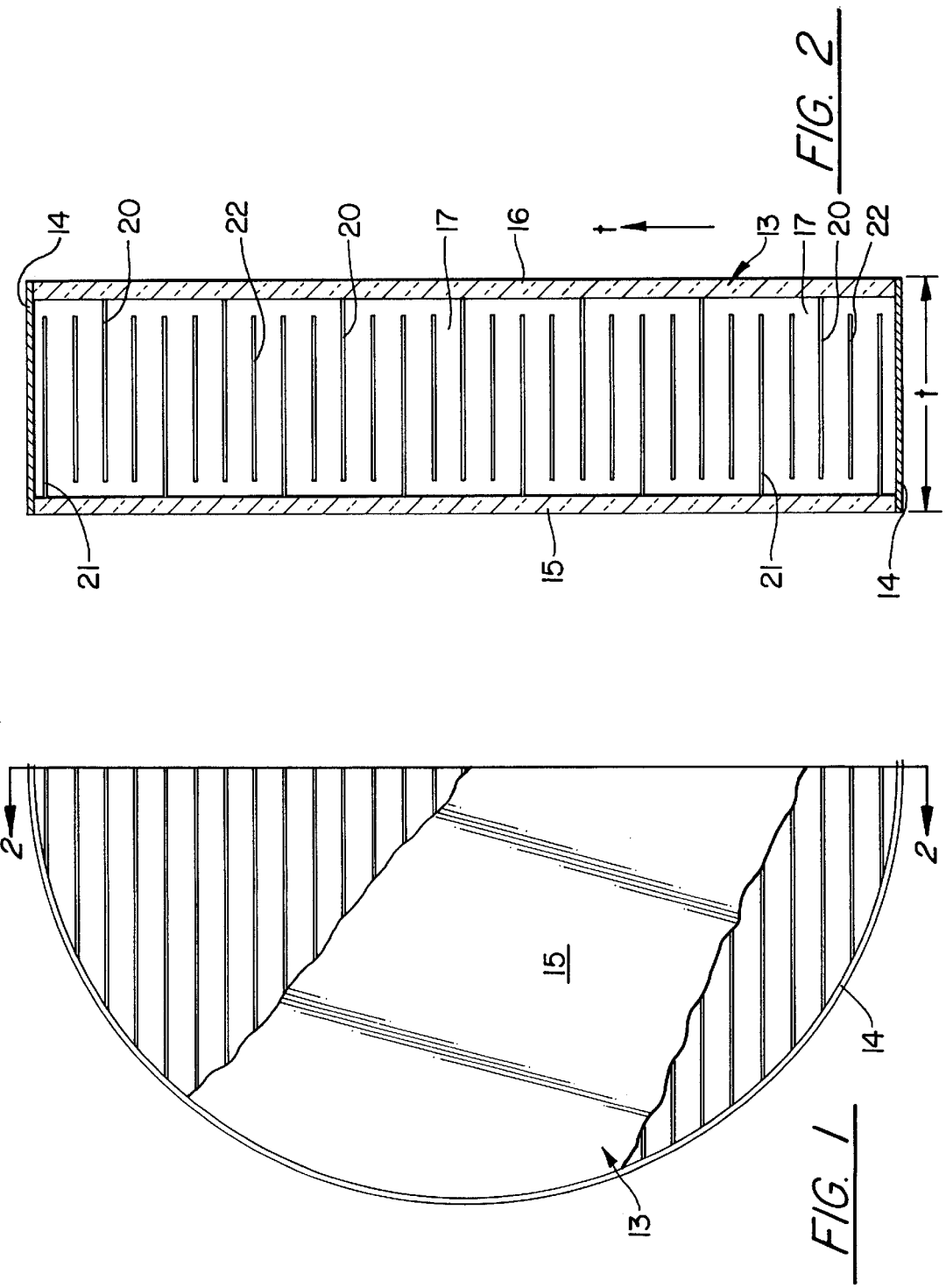

PROTECTING EYES AND INSTRUMENTS FROM LASER RADIATION

TECHNICAL FIELD

This invention relates to temperature induced phase shifts in segments of a protective lens, to cause power-dispersing thermal blooming.

BACKGROUND ART

Although many nations of the world have joined in a treaty to preclude the use of lasers as anti-personnel weapons, some of the more radical nations in the world may yet decide to use laser radiation as a weapon against individuals. There are numerous laser-operated weapon guidance devices, including target designators in which the target, such as an aircraft, is "painted" with laser radiation, and a guidance system homes in on that radiation. In either of these cases, it is quite possible that humans will be subjected to laser radiation sufficient to damage the eye. Furthermore, the onset of the laser radiation may be very sudden, giving insufficient time to prepare for it. In order to quantify, to some extent, the effects of high intensity laser radiation on human eyes, some of the following analysis utilizes data related to rabbits and monkeys presented by Birngruber et al, "Femtosecond Laser-Tissue Interactions: Retinal Injury Studies", IEEE Journal of Quantum Electronics, Volume QE-23, No. 10, October 1987, pp. 1836–1844. It is believed that the eye has an optical gain of anywhere from 20,000 to 100,000; that is, the intensity of radiation entering through the iris is amplified 20,000 to 100,000 times as it is focused on the retinal spot at the back of the eye. The retinal spot is on the order of 50 microns in diameter, or smaller, and it is understood that laser intensity of wavelengths between 4K Angstrom and 14K Angstrom of on the order of 2,000 watts per square centimeter, or more, will burn the retinal spot; that is, will permanently damage the retina to preclude vision. The human eye has a protection reflex which operates in about one-quarter second. Either the eye will close or the head will turn away from the irritating radiation in about that length of time. Therefore, one could anticipate that a weapon intentionally designed to blind personnel would have a wavelength which the eye will not respond to (that is, not between 8K Angstroms and 14K Angstroms) or if having a visible wavelength, will have suitable power to do all the necessary damage in less than one-quarter second. FIG. 12 of Birngruber, et al describes the dependence, in rabbits and monkeys, of retinal injury threshold upon laser pulse duration. That data, however, relates to intensity of radiation at the retina; due to the high gain of the eye, the intensity of radiation outside the eye to achieve the data referred to in the figure is less by a factor of between 20,000 and 100,000. Therefore, radiation of on the order of, say, thirty milliwatts per square centimeter entering the iris, over a duration as small as one microsecond, is sufficient to reach the threshold of permanent damage at the retina. This compares with one milliwatt per square centimeter which is deemed unsafe; that is, it is painful but not inducing permanent damage (American Standard Institute ANSI Z136.1-1993).

It is understood that all eye protection known to the art simply utilizes attenuation, in many cases wavelength selective attenuation, to tend to protect eyes while still permitting the eye to see something of interest. In the case of laser radiation discussed hereinbefore, the degree of attenuation in the visible range would have to be sufficiently great so as to totally preclude any ordinary, ambient light reaching the eye in the absence of the radiation from a laser. Of course, totally filtering, by attenuation, radiation outside the visible range would still leave the eye subject to intentional destruction by lasers in the visible range.

The foregoing analysis is applicable to non-living optical systems which have extremely high gain within their optical receiving systems. This includes a variety of instruments, such as satellite surveillance systems. As used herein, the terms "high gain optics" includes the human eye or eyes, and instruments which have significant optical gain and thereby may take advantage of the present invention.

Further, in the case of search or guidance instruments which are protected by narrow band filters having a center wavelength at the expected wavelength of a countermeasure of some sort, the countermeasure can switch wavelengths quite easily (such as by use of various isotopes of the lasing medium), thereby to mitigate the effectiveness of the filter. It is also known that a laser receptor protected by attenuators with narrow wavelength bands, in order to "see" in other portions of the visible spectrum, can be countermeasured easily, because all lasers can be shifted in wavelengths by large percents by various means such as isotopes of the lasing media, and therefore negate the attenuation protection.

DISCLOSURE OF INVENTION

Objects of the invention include protecting eyes and instruments against laser radiation, while hindering normal vision in the absence of laser radiation only to a tolerable degree; and provision of a laser protection lens which is light in weight and adaptable to a wide variety of optical situations, including periscopes, gun sights, target acquisition, search and tracking instruments, as well as ordinary eyeglasses. Another object of the invention is to protect eyes from harmful laser radiation while allowing meaningful sight of other images, even during periods of harmful irradiation.

According to the present invention, a lens for protecting optical systems having high optical gain, such as the human eye and optical instruments of high optical gain, induces thermal blooming of laser radiation passing therethrough by means of phase distortion in a plurality of segments normal to a plane passing through the optical axis of the lens.

According to the invention in one form, each segment is bounded on each side by a thermal sink. In one form, the thermal sink comprises a baffle wall of material, such as metal, having a relatively low thermal sensitivity to energy at laser wavelengths, and contains an aerosol of micron size particles, or laser absorbing gas, or a solid with submicron particles dispersed therein. The nature of the segment walls in the first form is generally not critical, and may be made as thick as is compatible with vision of the user, and as thin as is compatible with a sufficiently low temperature rise (when irradiated) and with structural integrity. Each segment, in gaseous embodiments, may allow free passage of aerosol or gas from one to the next, the sector walls serving only to clamp the temperature suitably below the temperature of particles in the aerosol or gas midway between the walls, rather than as containment.

According to the invention in another form, each segment comprises a varying length of an absorption material. In one form, this may comprise one wavelength (or quasi wavelength) of a spatially periodic (or non-periodic, randomly varying) boundary of an aerosol of micron size particles or a gas, or a solid with submicron particles. According to the invention, the aerosol contains particles such as carbon soot, silica, or alumina, having a major dimension (radius, if round) on the order of a micron. The size may, however, depend in part on other constraints such as lifetime of suspension, absorption efficiency at a particular wavelength, and/or compatibility with the glass system or other lens materials. Or, gases such as ozone, nitrous oxide and ethylene may be used. Or a solid glass or plastic may have carbon soot or other materials dispersed therein.

According to the invention in another form, each segment comprises a portion of lens having a maximal density of an absorption medium bounded by portions having little or no absorption medium; in other words; the lens constitutes a spatially periodic (or non-periodic, randomly varying) variation in the density of absorption material.

In other words, the invention may be practiced by providing temperature differentials in a uniform absorption medium, varying length of a maximal absorption medium, or variations in the density of absorption medium.

In still further accord with the invention, each eye is protected by a lens having its phase distortion oriented normal to that of the other lens, which utilizes the unique capabilities of the human brain to provide meaningful composite images during periods of high intensity laser radiation, without incurring any damage to the retinae of the eyes.

In accordance with one embodiment of the invention, each sector may be on the order of one centimeter in length (parallel to the optical axis of the lens), with a width on the order of a quarter centimeter. The sectors may be bounded by totally transparent lens sections at either end, when appropriate, but need not be in all cases.

Other objects, features and advantages of the present invention will become more apparent in the light of the following detailed description of exemplary embodiments thereof, as illustrated in the accompanying drawing.

BRIEF DESCRIPTION OF THE DRAWINGS

FIG. 1 is a partial, front elevation view of a cell in accordance with the present invention.

FIG. 2 is a section side elevation view taken on the line 2—2 of FIG. 1.

BEST MODE FOR CARRYING OUT THE INVENTION

Figure 3:
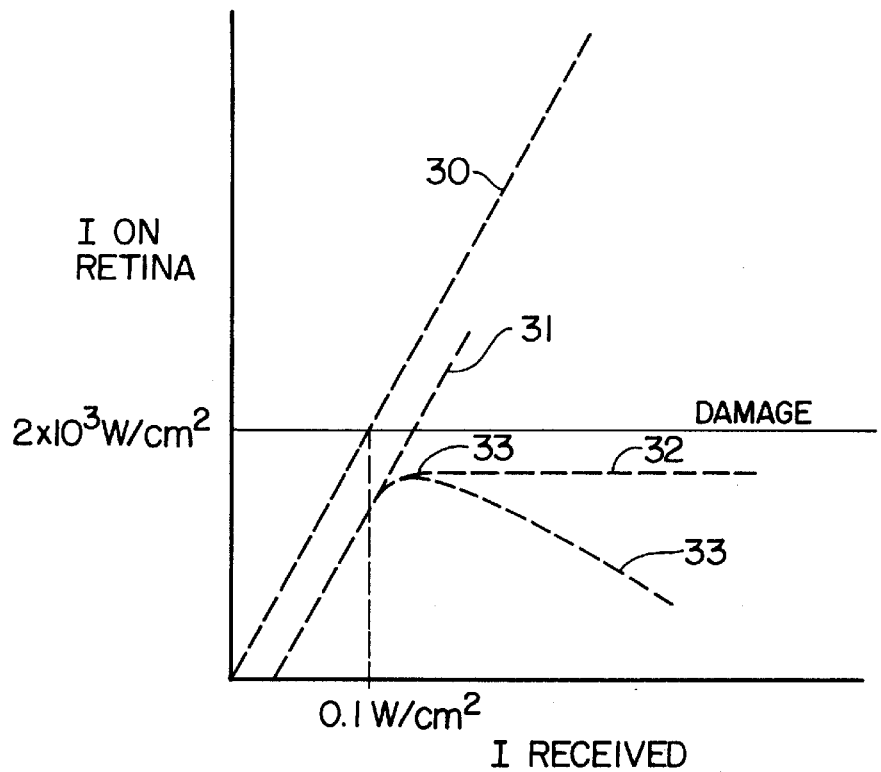
FIG. 3 is a graphical illustration of the intensity of radiation on the retina as a function of intensity of radiation passing through the eye, both without the invention and with the invention.

Referring to FIGS. 1 and 2, a cell 13 in accordance with the present invention comprises a cylinder 14 having a diameter on the order of 40 or 50 millimeters and a thickness, t (side-to-side in FIG. 2), on the order of 9 millimeters. The cylinder 14 is enclosed on either side by transparent lenses 15, 16 so as to provide a fully enclosed cell. In the space 17 within the cell 13 there is a high density aerosol of micron size particles. The particles should be small so as to remain suspended but large enough to have an efficiency of light absorption leading to gas heating. A preferred size is about one tenth of a micron, but the size may range from 0.01 microns to 100 microns. The particles may preferably be selected from among particles having a high absorption and long suspension lifetime characteristics, such as carbon soot, silica, and alumina. The density of particles should be on the order of $10^7$ particles per cubic centimeter within the space 17 between the lenses 15, 16. A plurality of baffles 20–22 are supported by the cylinder 14. The baffles 17–22 may touch the lens 16, as do the baffles 20, they may touch neither of the lenses as is true of the baffles 22, or they may touch the lens 15, as is true of the baffles 21. However, it is believed best to not contain the particles between any pair of baffles, but rather to allow the particulate density to remain substantially uniform throughout the lens 13, and therefore to have free flow of particles from the space between one set of baffles to the adjacent space, throughout the lens 13. The baffles are mutually parallel and parallel with the optical axis of the lens. They may be separated by about a quarter centimeter.

FIG. 3 illustrates the intensity of radiation on the retina as a function of the intensity of radiation that passes through the iris. As described hereinbefore, since there is on the order of 20,000 to 100,000 gain within the eye itself, it takes only on the order of 30 milliwatts per square centimeter entering the eye to result in the damage-intensity-level of 2,000 watts per square centimeter at the retina, as illustrated by the dashed line 30 which comprises a plot of the gain of the eye. If, in accordance with the invention, the intensity of radiation is reduced by attenuation, the intensity being passed through the eye to the retina might follow the dashed line 31. However, in addition to attenuation, the present invention provides periodic phase shift across the cell, and therefore across one dimension of the iris, and the result is an absolute limit upon the amount of radiation that will focus on the retina of the eye as indicated by the dashed line 32 in FIG. 3. The amount of intensity that focuses on the retina is essentially constant because the phase shift, and therefore the increase in beam divergence, is linear with respect to power and exactly balances the increase in laser power. Therefore, for each increment of increased radiation, there is a linearly corresponding incremental increase in the dispersion thereof, causing the intensity that focuses on the retina to be independent of the power, above some power threshold, such as the point 33 on the dashed line 32 in FIG. 3.

Figure 4:
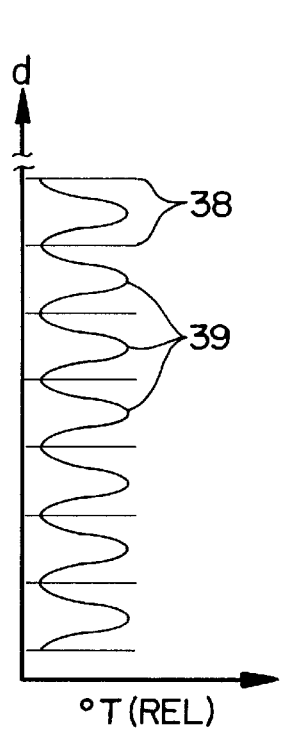
FIG. 4 is a graph illustrating temperature of the gas in the cell of FIG. 1 as a function of distance across the cell under intense radiation.

In FIG. 4, the horizontal lines 38 are indicative merely of the spacing of the baffles 20–22 in FIGS. 1 and 2. The waveforms are a plot of temperature as a function of distance, d, across the cell. The baffles have a tendency to remain cooler than the gas in between; additionally, the gas adjacent to the baffles tend to be at the temperature of the baffles. The temperature of the gas caused by aerosol absorption midway between the baffles is higher than the temperature of the gas closer to the baffles. This is illustrated by the waveform 39. The temperature differential between the aerosol midway between the baffles and the aerosol adjacent to the baffles need be as little as one degree, in order for the invention to work. The change in phase, is:

$$\Delta \phi = \frac{2\pi}{\lambda} \Delta T \mu_T R \qquad \text{EQN. 1}$$

where $\Delta T$=temperature change, $\mu_T$ is the change in index of refraction with temperature and R the propagation range.

Figure 5:
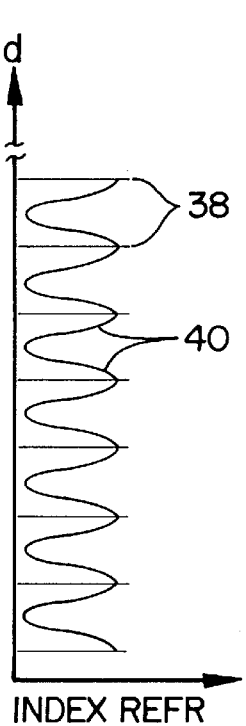
FIG. 5 is a graph illustrating index of refraction as a function of distance across the cell of FIG. 1, resulting from temperature gradients of FIG. 4.

A phase change of one degree will provide an index of refraction change on the order of one wavelength for a one centimeter path. This results in gradients in index of refraction which are maximal midway between the baffles, and is minimal adjacent to the baffles, as illustrated by the plot on FIG. 5. The resulting change in phase, $\phi$, is:

$$\Delta \phi = \frac{2\pi}{\lambda} \int_0^D \Delta \mu dT \qquad \text{EQN. 2}$$

where $\phi$=phase, $\lambda$=wavelength, and

T=distance through the cell.

Figure 6:
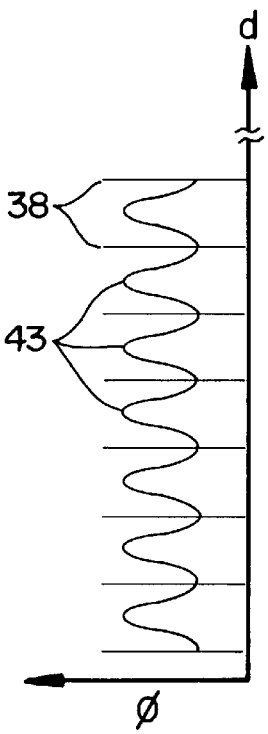
FIG. 6 is a graph indicating phase angle of radiation as a function of distance across the cell of FIG. 1 which results from the variation in index of refraction illustrated in FIG. 5.

As is known, the phase of radiation will be altered differently as it passes through equal lengths of a different index of refraction, resulting in phase differentials which are greatest midway between the baffles as illustrated by the plot 43 in FIG. 6. Thus, the radiation will enter the cell 13 with essentially uniform intensity and phase, but will leave the cell 13 with a spatially periodic phase difference, as seen in FIG. 6, which causes wide dispersion of the radiation, thereby decreasing its spatial intensity well below that which can cause damage to the retina.

The intensity, I, is power, P, per unit area; for radiation focused in a circular spot of radius "a", $$I = \frac{P}{\pi a^2} \qquad \text{EQN. 3}$$

For radiation defocused in one axis, into a roughly elliptical shape having dimensions a, b, $$I = \frac{P}{\pi ab} \qquad \text{EQN. 4}$$

Therefore, if the defocus mechanism were operative in two, orthogonal axes, the intensity would decrease with the square of the mechanism as shown by the dotted line 33 in FIG. 3; in this case, with the square of phase change.

Figure 7:
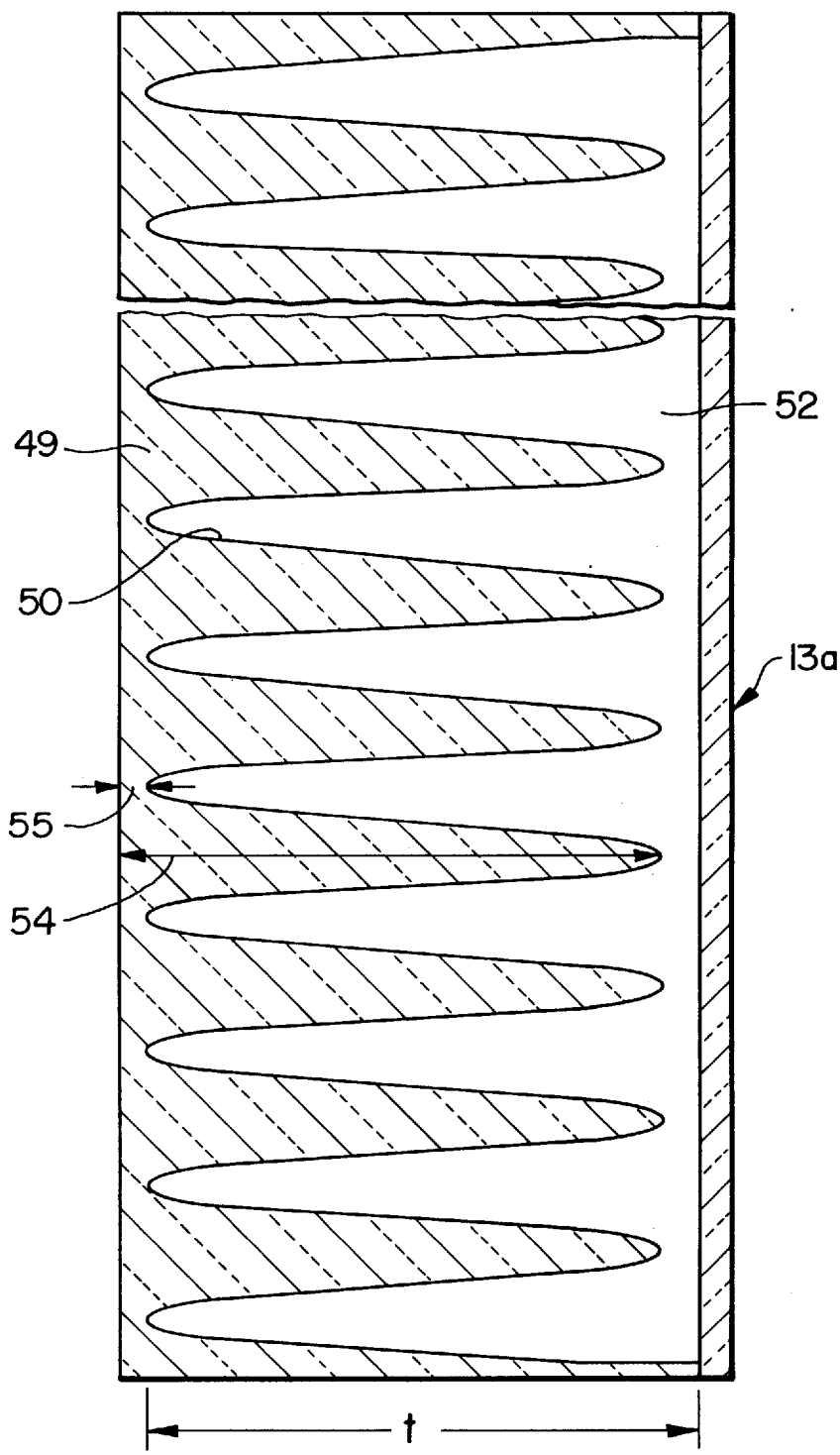
FIG. 7 is a side elevation view of a second embodiment of the invention.

In the embodiment of FIG. 7, the cell 13a has a glass or plastic structure 49 with a quasi-sinusoidal, serpentine surface 50 which defines a chamber 52 that contains a very high density aerosol. Therefore, under intense radiation, the temperature of the gas in the chamber 52 will become quite high which causes a change in the index of refraction, and in turn results in a change in the phase of any radiation passing through the cell. The amount of phase change will be a function of the length of path through which the radiation passes. Therefore, there will be a greater phase change for radiation passing through the path 54 than there will for the path 55. Thus, there will be the same sort of phase change as a function of distance, t, as is described with respect to FIG. 6, hereinbefore. But in this instance, it is caused by a difference in distance of optical path at a same temperature, whereas in the cell of FIGS. 1 and 2, it is achieved by different temperatures having the same path length.

An extension of the embodiments of FIGS. 1 and 7 is to utilize specific gases, rather than aerosols, to cause the heating and commensurate change in the index of refraction in order to result in a phase change. As an example, ozone, $O_3$, has high absorption for wavelengths between 4K Angstroms and about 6K Angstroms; nitrous oxide, $NO_2$, has good absorption for wavelengths between about 6K Angstroms and 8K Angstroms; and ethylene $C_2H_4$ has good absorption for wavelengths between 6K Angstroms and 14K Angstroms. Therefore, a mixture of these gases in the chamber 52 will provide results similar to those described with respect to FIGS. 1 and 7 hereinbefore, and will provide the additional advantage of having no concern over maintaining suspension of particles. Additionally, if desired, the relative density of the three gases may be proportioned inversely with their absorption characteristic at the desired wavelengths so as to provide a relatively uniform phase change as a function of wavelength. However, since the intention here is to spread the intensity, all that matters is that it be spread sufficiently, and therefore uniformity is not needed.

Figure 8:
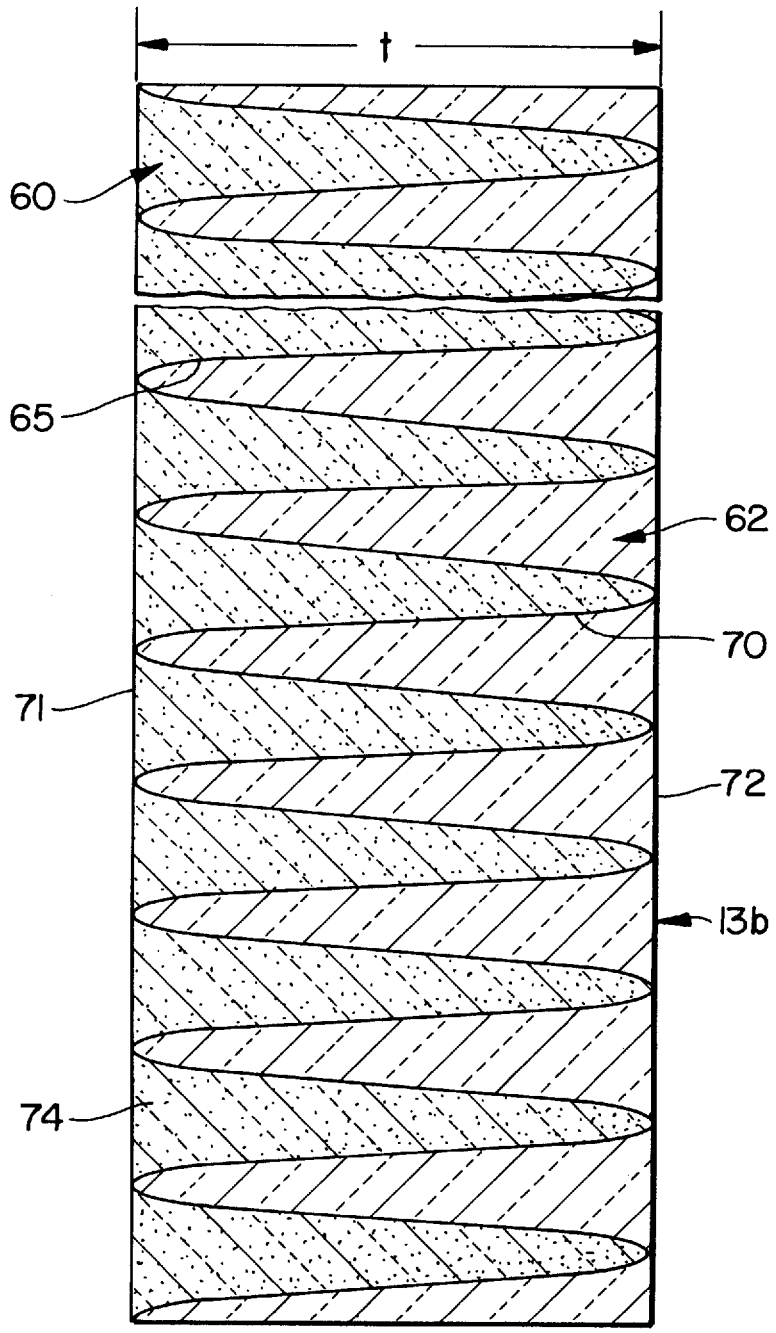
FIG. 8 is a side elevation view of a third embodiment of the invention.

Referring now to FIG. 8, an extension of the embodiment of FIG. 7 utilizes substantially transparent glass or plastic, one part 60 having micron size particles 61, such as carbon soot, dispersed therein, and the other part 62 having no particles dispersed therein. Except for the particles, the materials of the parts 60, 62 are identical. As used herein, the term "substantially transparent" means sufficiently transparent to normally conduct optical radiation needed by the high gain optics—e.g., to permit vision as we know it; the transparency may range from totally clear to the transmissivity of dark sunglasses. The part 60 can be formed by being poured in a mold which has a wavy surface (similar to the wall in the embodiment of FIG. 7) so as to provide a serpentine surface 65 on the part 60. Then additional material can be poured onto the surface 65 so as to form the portion 62. As in the embodiment of FIG. 7, the difference in phase stems from the difference in thickness, t, that radiation traverses through the portion 60, depending upon what part of the wavy surface it passes through. The portion 60 may be made utilizing other particles mentioned hereinbefore. In FIG. 8, the serpentine surface 65 extends from one surface 71 to the other surface 72 of the lens so that the entire thickness of the lens is involved with the change in temperature, index of refraction, and phase. In FIG. 8, the stippled part 60 preferably comprises allyl diglycol carbonate (a plastic commonly used in eyeglasses) with particles of carbon soot dispersed therein in a density level sufficient to provide some absorption, perhaps on the order of that found in dark sunglasses. The non-stippled part 62 of the lens in FIG. 8 is the same material but without the carbon particles. If the wavelength (from trough to trough) of the interface 65 is on the order of a quarter of a centimeter, a thickness, t, on the order of about one centimeter (from right to left in FIG. 8) will be sufficient to provide a phase shift which will disperse optical energy so as to reduce the energy on the retinal spot to about one and one-half kilowatts per square centimeter, which is below the two kilowatts per square centimeter referred to hereinbefore as permanently damaging the eye.

The embodiment of FIG. 8 could of course be practiced utilizing some other plastic, or glass, as the medium, and other materials such as silica or alumina may be used for seeding the medium to provide the necessary heat absorption, change in index of refraction and commensurate phase shift.

In FIG. 8, the interface extends between surfaces 71, 72; one being the optical entry surface and the other being the optical exit surface; of course, the interface need not extend completely between said two surfaces, if desired; it suffices if the interface extends substantially between the two surfaces.

Figure 9:
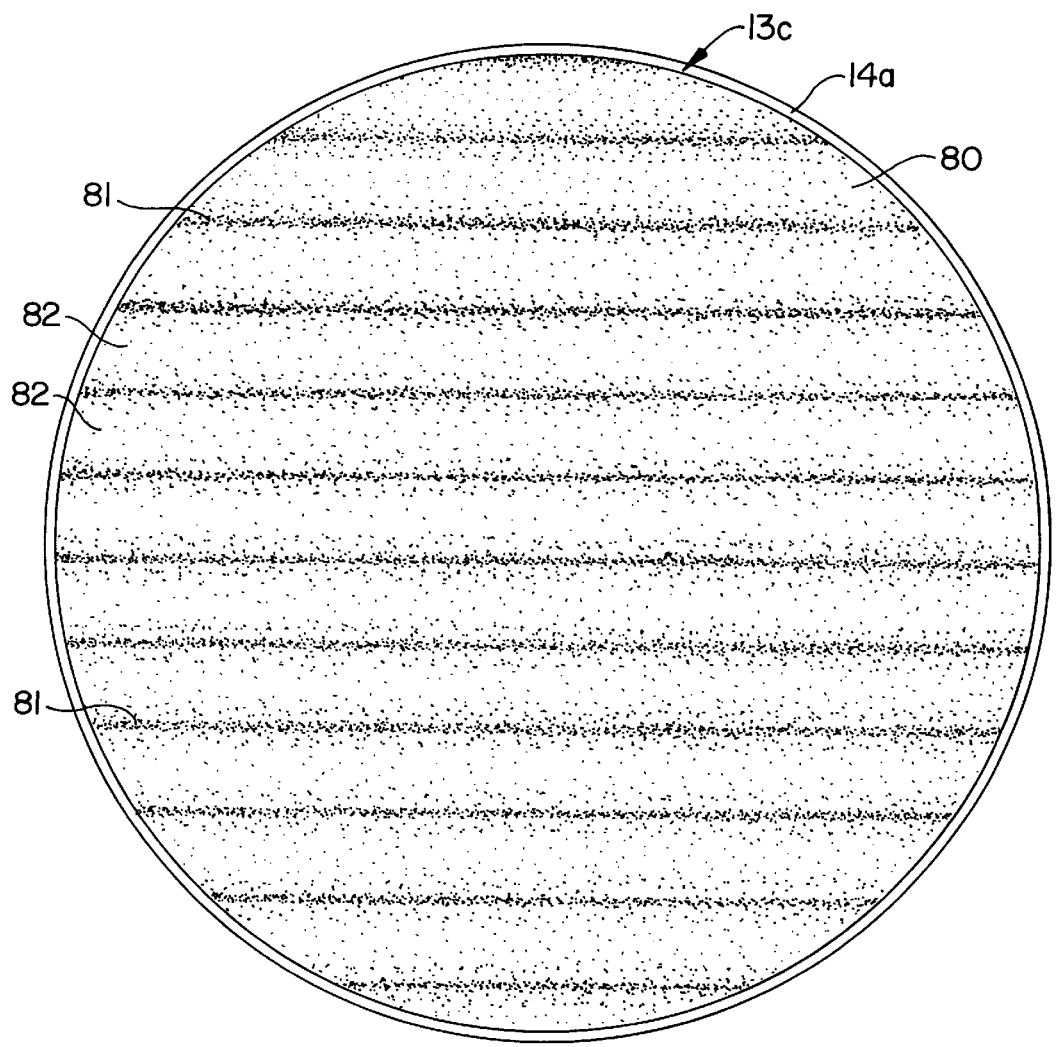
FIG. 9 is a side elevation view of a fourth embodiment of the invention.

Referring now to FIG. 9, another embodiment of a lens 13c may comprise a cylinder 14a, the inside of which is filled with ADC, glass or other material 80 having absorption material, such as carbon soot, silica or alumina of varying density; the peaks 81 and troughs 82 of density are indicated by the density of stippling therein. This could be formed from the bottom up (as is seen in FIG. 9) by pouring successive layers of material having premixed desired density of absorption material therein, in an obvious fashion. The troughs may be spaced by about a quarter of a centimeter.

Although the embodiments hereinbefore portray smooth variations in characteristics (e.g., sinusoidal), the characteristics need not vary in a smooth fashion, but may have step function changes therein and still be equally as effective in causing the distortion which is required to achieve thermal blooming. Similarly, in the embodiment of FIG. 9, layers of four or five different densities of absorption material may be laid up to provide a pattern which will achieve suitable distortion. In fact, the invention may be practiced by simply providing sandwiches of four or five different materials, each having a different density of absorption material so as to achieve a periodic absorption effect thereby to achieve the phase change required for thermal booming.

In accordance with another aspect of the invention, lenses within the optical path of each eye are oriented so that the phase distortion of one of them is 90° relative to the phase distortion of another of them. Simply stated, the baffles of FIG. 1 will be vertical in one lens and horizontal in the other; similarly, the troughs in FIGS. 7 and 8 and the density pattern of FIG. 9 will be vertical in one lens and horizontal in the other. In each case, radiation of a threshold intensity will cause the heating which provides a uniform transmissibility of that radiation to the retina, as described hereinbefore. In such case, the eye would see relatively low levels of that radiation; however, such relatively low level of radiation is uniform across the entire vision field of the eye. In the case of selected patterns of varying colors of radiation, such as from cockpit instruments or a head-up display, the radiation entering each eye will be focused in either one direction or the other, but not both. Either eye will see simply images compressed into almost a single line; one eye seeing a vertical line and the other eye seeing a horizontal line. The brain will take the focused radiation from the two eyes and put them into a single image so that the information conveyed by images of radiation of different wavelengths can be discerned by the brain. This effect is similar to one that can be observed by looking through two cylinders of glass filled with water (or some other material having an index of fraction different from that of air) at the same time: if one of the glasses has its axis extending vertically and the other has its axis extending horizontally, then each eye will see essentially nothing, but both eyes together will see a somewhat degraded version of the image that the naked eyes together would see. Therefore, a pilot, for instance, wearing goggles of the present invention having the phase distortion oriented vertically in front of one eye and oriented horizontally in front of the other eye will still be able to read instruments and images in the cockpit, even while being bathed in laser light that has induced the mechanism of the present invention to create the intensity-reducing phase change. This is an important feature of the present invention.

In implementing the present invention, selection among the various embodiments disclosed herein made be made based upon the particular utilization to which the invention is to be put. Embodiments using a gaseous medium, such as an aerosol with absorbing particles or gases which have good absorption characteristics, have a rapid response time. On the other hand, an aerosol may have difficulty maintaining its usefulness over a long shelf life. The solid embodiments, such as glass or plastic, are easy to manufacture and have a very long life time. In the embodiments using fins, the lens can be fabricated by sandwiching solid glass or plastic material between the metal fins. On the other hand, the thin structure may be supported (as with a temporary comb arrangement) and liquid glass or plastic, having suitable particulates, poured therein. The gaseous embodiments employing fins may have a structural integrity problem, and be less useful for certain high-shock environments. The embodiments having solid medium may, on the other hand, have a slower thermal response time, and thereby not provide protection until the elapse of 60 milliseconds or more.

In the solid embodiments, glass or plastics other than ADC may be used. However, ADC is preferred because it has (1) poor thermal conductivity, yielding high temperature gradients; (2) high index of refraction, for maximal phase distortion per unit thickness; and (3) light weight.

As used herein, the term "periodic" means reaching successive maxima and minima across successive spatial periods of either unequal or equal dimensions. In fact, since distortion is the goal, a random or near-random variation in temperature, length or density may be preferred.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A method of protecting optical systems having optical gain and an optical axis from harmful laser radiation which comprises providing, at the optical entry to said optical system, a medium having an index of refraction which varies spatially periodically along one dimension perpendicular to said optical axis in response to said radiation, thereby to induce a periodic phase change in said radiation, whereby said radiation will be defocused along said one dimension.

2. A method according to claim 1 which comprises providing said medium with a temperature rise which is periodic along said one dimension in response to said radiation.

3. A method according to claim 2 which includes providing a plurality of periodically dispersed baffles having a temperature coefficient of absorption which is lower than said medium, whereby said baffles will remain at a temperature cooler than the medium between said baffles, thereby to provide periodicity in the temperature of said medium.

4. A method according to claim 1 which comprises providing said medium with a dimension parallel to said optical axis which varies periodically in said one dimension, whereby the path length of altered index of refraction is periodic, thereby inducing a periodic phase change in radiation emerging from said medium.

5. A method according to claim 1 which comprises providing said medium with a characteristic of absorption of said radiation which varies periodically in said one dimension.

6. A method according to claim 1 wherein said optical system comprises a pair of eyes of a human being and said method comprises inducing a periodic phase change for one eye which is perpendicular to the periodic phase change induced for the other eye.

7. A lens for protecting optics having optical gain from laser radiation comprising:

a substantially transparent chamber having an optical axis, said optical axis coaligned substantially with the optical axis of the optics to be protected by said lens;

a plurality of mutually parallel planar baffles disposed within said chamber, said baffles being parallel with said optical axis; and a medium in said chamber having a characteristic of absorption of radiation of wavelengths within the spectrum of wavelengths from which said optics is to be protected.

8. A lens according to claim 7 wherein said medium comprises aerosol containing particles on the order of a micron in size.

9. A lens according to claim 7 wherein said particles are selected from the group consisting of carbon soot, silica and alumina.

10. A lens according to claim 7 wherein said medium is a gas having micron size particles dispersed therein.

11. A lens according to claim 10 wherein said particles are selected from the group consisting of carbon soot, silica and alumina.

12. A lens according to claim 7 wherein said medium comprises a mixture of gases which together have an absorption characteristic for radiation within the spectrum of radiation from which said lens is to protect said optics.

13. A lens according to claim 12 wherein said mixture includes ozone, nitrous oxide and ethylene.

14. A lens for protecting optics having optical gain and an optical axis from laser radiation, said lens having an optical axis which is coaligned with the optical axis of said optics and having an optical entry surface and an optical exit surface, comprising:

a first portion, said first portion formed of a medium; and a second portion, said second portion formed of said medium with micron size particles suspended therein;

said portions being separated by a serpentine interface, said interface having troughs which are normal to said optical axis.

15. A lens according to claim 14 wherein said interface extends substantially between said entry and exit surfaces.

16. A lens according to claim 14 wherein said medium is plastic.

17. A lens according to claim 16 wherein said medium is allyl diglycol carbonate.

18. A lens according to claim 14 wherein said medium is glass.

19. A lens according to claim 14 wherein said particles are selected from the group consisting of carbon soot, silica and alumina.

20. A lens for protecting optics having optical gain and an optical axis from laser radiation, said lens having an optical axis which is coaligned with the optical axis of said optics and having an optical entry surface and an optical exit surface, comprising:

a first portion formed of a medium, a first surface of which comprises one of said optical surfaces and a second surface of which has a serpentine shape with troughs which are normal to said optical axis;

a lens formed of said medium, said lens being disposed on said first portion to form a chamber, one surface of said lens forming the other of said optical surfaces, the other surface of said lens opposite to said one surface forming a surface of said chamber opposite to said serpentine surface; and a gaseous medium in said chamber having a characteristic of absorption of radiation of wavelengths within the spectrum of wavelengths from which said optics is to be protected.

21. A lens according to claim 20 wherein said gaseous medium is a gas having micron size particles dispersed therein.

22. A lens according to claim 21 wherein said particles are selected from the group consisting of carbon soot, silica and alumina.

23. A lens according to claim 20 wherein said gaseous medium comprises a mixture of gases which together have an absorption characteristic for radiation within the spectrum of radiation from which said lens is to protect said optics.

24. A lens according to claim 23 wherein said mixture includes ozone, nitrous oxide and ethylene.

25. A lens for protecting optics having optical gain and an optical axis from laser radiation, said lens having an optical axis which is coaligned with the optical axis of said optics and having an optical entry surface and an optical exit surface, said lens comprising a medium with micron size particles suspended therein in a pattern of density variations, said density variations repetitively varying between peaks of maximal density and troughs of minimal density, said peaks and troughs being normal to said optical axis.

26. A lens according to claim 25 wherein said medium is plastic.

27. A lens according to claim 26 wherein said medium is allyl diglycol carbonate.

28. A lens according to claim 25 wherein said medium is glass.

29. A lens according to claim 25 wherein said particles are selected from the group consisting of carbon soot, silica and alumina.

30. Eyeglasses, having a pair of optical axes, for protecting human eyes from harmful laser radiation, comprising:

a first lens for one eye, said first lens responding to radiation within the spectrum of radiation from which said eyes are to be protected to provide an index of refraction which varies spatially periodically across one dimension of said first lens perpendicular to said axis, thereby to induce thermal blooming of said radiation in said one dimension; and a second lens for the other eye, said second lens responding to radiation within the spectrum of radiation from which said eyes are to be protected to provide an index of refraction which varies spatially periodically across a second dimension of said second lens which is perpendicular to both said one dimension and to said axis, thereby to induce thermal blooming of said radiation in said second dimension.

31. A lens for protecting optics having optical gain and an optical axis from laser radiation, said lens having an optical axis which is coaligned with the optical axis of said optics, comprising:

an optical entry surface and an optical exit surface; and a medium, disposed between said entry surface and said exit surface, having an index of refraction which varies spatially periodically along one dimension perpendicular to said optical axis in response to said radiation, thereby to induce a periodic phase change in said radiation, whereby said radiation will be significantly defocused along said one dimension.

* * * * *